United States Patent [19]

Kameswaran et al.

[11] Patent Number: 5,194,630
[45] Date of Patent: Mar. 16, 1993

[54] PROCESS FOR THE MANUFACTURE OF INSECTICIDAL 2-ARYL-1-(ALKOXYMETHYL)-4-HALO-5-(TRIFLUOROMETHYL)PYRROLES

[75] Inventors: Venkataraman Kameswaran, Princeton Junction; Robert F. Doehner Jr., East Windsor, both of N.J.

[73] Assignee: American Cyanamid Company, Stamford, Conn.

[21] Appl. No.: 634,288

[22] Filed: Dec. 26, 1990

[51] Int. Cl.$^5$ .................. C07D 207/34; C07D 207/42; C07B 39/00; A01N 43/36
[52] U.S. Cl. .................................... 548/561; 548/531; 548/526
[58] Field of Search .................. 548/526, 531, 561

[56] References Cited

U.S. PATENT DOCUMENTS 4,929,634  5/1990  Herman .......................... 514/426

FOREIGN PATENT DOCUMENTS 0279716  8/1988  European Pat. Off. .
0281707  9/1988  European Pat. Off. .
0347488  12/1989  European Pat. Off. .
0358047  3/1990  European Pat. Off. .

Primary Examiner—Mark Berch
Attorney, Agent, or Firm—Peggy A. Climenson

[57] ABSTRACT

There is provided a process for the manufacture of insecticidal 2-aryl-4-halopyrrole compounds via the in situ sequential oxidation, ring halogenation and side chain halogenation of an appropriate 2-aryl-1-methyl-2-pyrroline precursor.

9 Claims, No Drawings

PROCESS FOR THE MANUFACTURE OF INSECTICIDAL 2-ARYL-1-(ALKOXYMETHYL)-4-HALO-5-(TRI-FLUOROMETHYL)PYRROLES

BACKGROUND OF THE INVENTION

Certain substituted arylpyrrole compounds and their use as insecticidal, acaricidal and nematocidal agents are described in copending U.S. application Ser. No. 392,495 filed on Aug. 11, 1989 which is a continuation-in-part of U.S. application Ser. No. 208,841 filed on Jun. 23, 1988 which is a continuation-in-part of U.S. application Ser. No. 079,545 filed on Jul. 29, 1987, now abandoned. Although 4-chloro-1-(ethoxymethyl)-2-(p-chlorophenyl)-5-(trifluoromethyl)pyrrole-3-carbonitrile, 4-chloro-1-(chloromethyl)-2(p-chlorophenyl)-5-(trifluoromethyl) -pyrrole-3-carbonitrile and 4-bromo-1-(bromomethyl)-2-(p-chlorophenyl)-5-(trifluoromethyl)pyrrole-3-carbonitrile compounds are found within the broad generic description of said application, said pyrrole-3-carbonitrile compounds are not specifically named, described or exemplified therein.

A process for the preparation of 2-aryl-1-(unsubstituted)-5-(trifluoromethyl)pyrrole compounds via an azalactone intermediate is described in copending U.S. application Ser. No. 560,396 filed on Jul. 31, 1990.

It is an object of this invention to provide a process for the manufacture of 4-halo-2-aryl-1-(alkoxymethyl)-5-(trifluoromethyl)pyrrole compounds which are useful for controlling insect, acarid and nematode pests and for protecting harvested and growing crops from said pests.

It is another object of this invention to provide intermediate 4-halo-2-aryl-1-(halomethyl)-5-(trifluoromethyl)pyrrole compounds.

It is a further object of this invention to provide an insecticidal, acaricidal and nematocidal agent 4-chloro-1-(ethoxymethyl)-2-(p-chlorophenyl)-5-(trifluoromethyl)pyrrole-3-carbonitrile and a method for its use to protect harvested and growing crops.

SUMMARY OF THE INVENTION

This invention is directed to a process for the manufacture of insecticidal arylpyrrole compounds of formula I

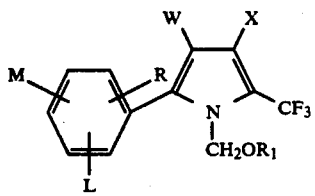

wherein
$R_1$ is $C_1$-$C_6$ alkyl;
W is CN, $NO_2$ or $CO_2R_2$;
X is Br, Cl or I;
L is hydrogen or halogen;
M and R are each independently hydrogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, CN, $NO_2$, Cl, Br, F, I, $CF_3$, $R_3CF_2Z$, $R_4CO$ or $NR_5R_6$ and when M and R are on adjacent positions they may be taken together with the carbon atoms to which they are attached to form a ring in which MR represents the structure —$OCH_2O$—, —$OCF_2O$— or
—CH=CH—CH=CH—;

$R_2$ is $C_1$-$C_6$ alkyl, $C_3$-$C_6$ cycloalkyl or phenyl;
$R_3$ is hydrogen, F, $CHF_2$, CHFCl or $CF_3$;
$R_4$ is $C_1$-$C_4$ alkyl, $C_1$-$C_4$ alkoxy or $NR_5R_6$;
$R_5$ is hydrogen or $C_1$-$C_4$ alkyl;
$R_6$ is hydrogen, $C_1$-$C_4$ alkyl or $R_7CO$;
$R_7$ is hydrogen or $C_1$-$C_4$ alkyl;
Z is $S(O)_n$ or O and
n is an integer of 0, 1 or 2 which comprises reacting a compound of formula II

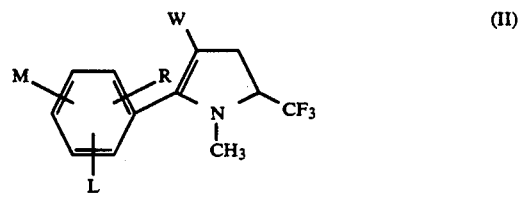

wherein W, L, M and R are as described hereinabove, with at least 1 molar equivalent of a halogen, $X_2$, wherein $X_2$ is Br, Cl or I, preferably at an elevated temperature in the presence of a solvent to obtain a 2-aryl-1-methylpyrrole intermediate, reacting said 1-methylpyrrole intermediate with at least one additional molar equivalent of said halogen to form a 2-aryl-4-halo-1-methylpyrrole intermediate, reacting said 4-halo-1-methylpyrrole intermediate further with at least one molar equivalent of said halogen in the presence of a radical initiator to form a 2-aryl-4-halo-1-(halo-methyl)-pyrrole intermediate and reacting said 4-halo-1-(halomethyl)pyrrole intermediate with at least one molar equivalent of an alkali metal $C_1$-$C_6$alkoxide to give the compound of formula I.

The compounds of formula II and a method for the preparation thereof are described in copending U.S. application Ser. No. 07/634,287 U.S. Pat. No. 5,118,816 filed concurrently herewith and incorporated herein by reference thereto.

DESCRIPTION OF THE INVENTION

The compounds of formula I are particularly effective for controlling insect, acarid and nematode pests and for protecting agronomic crops, both growing and harvested, against the ravages of these pests. Methods of preparation for the compounds generally include halogenation of 2-aryl-5-(trifluoromethyl) -pyrrole-3-carbonitrile with a halogenating agent such as a hypohalite, a halogen or a sulfurylhalide to form the corresponding 4-halopyrrole intermediate and alkylating said intermediate with an appropriate chloromethyl($C_1$-$C_6$ alkyl)ether.

It has now been found that compounds of formula I, particularly wherein X is chlorine, may be readily and efficiently manufactured from pyrroline compounds of formula II by the incremental addition of the appropriate halogen in the presence of a solvent preferably at an elevated temperature to form a 4-halo-1-methylpyrrole intermediate of formula III, the in situ reaction of formula III intermediate with additional halogen in the presence of a radical initiator to form a 4-halo-1-

(halomethyl)pyrrole intermediate of formula IV and the reaction of formula IV intermediate with an alkali metal $C_1$–$C_6$alkoxide. Surprisingly, the desired compounds of formula I are obtained in good yields and have a high degree of purity. The process of the present invention is shown in flow diagram I.

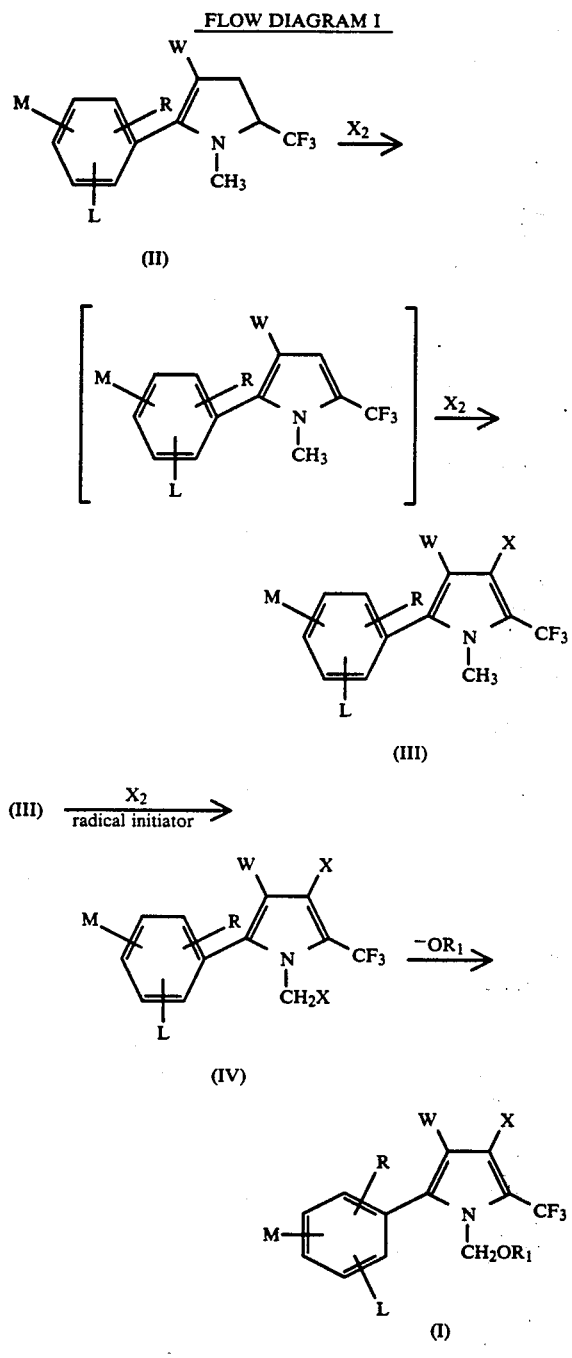

Advantageously, it has been found that the incremental addition of halogen improves the reaction yield and product purity. The process of the invention also improves the environmental and human safety of the manufacture of compounds of formula I by avoiding the use of certain undesirable reactants such as chloromethylethylether. Further, the process of the invention includes the productive manufacture of 2-(p-chlorophenyl) -4-chloro-1-ethoxymethyl-5-(trifluoromethyl) -pyrrole-3-carbonitrile, an effective insecticidal, acaricidal and nematocidal agent.

Solvents suitable for use in the process of the present invention include aprotic solvents, for example halogenated aromatic hydrocarbons such as chlorobenzene, o-dichlorobenzene and the like and halo-genated hydrocarbons such as methylene chloride, carbon tetrachloride, chloroform, 1,2-dichloroethane and the like. Preferred solvents include halogenated aromatic hydrocarbons such as chlorobenzene and halogenated hydrocarbons such as carbon tetrachloride. Radical initiators suitable for use are light, peroxides such as dibenzoyl peroxide, di-t-butylperoxide, and the like; azo compounds such as azobisisobutyronitrile and the like. Among the preferred radical initiators are benzoyl peroxide and light. Alkali metal alkoxides suitable for use in the inventive method are sodium ethoxide, potassium methoxide and the like.

In the process of the invention the reaction rate is increased with increased temperature so that elevated temperatures in the range of about 55° to 210° C., preferably about 70° to 120° C., allow the oxidation, ring halogenation and side chain halogenation to proceed at an efficient and effective rate without causing undue adverse side reactions.

It is now apparent that the process of the invention includes the operative manufacture of an insecticidal, acaricidal and nematocidal agent, 2-(p, chlorophenyl)-4-chloro-1-(ethoxymethyl)-5-(trifluoromethyl)pyrrole-3-carbonitrile. The pyrrole-3-carbonitrile is effective for controlling acarina, lepodoptera, colioptera, hemiptera and the like. Among the agronomic pests that may be effectively controlled are potato beetle, cabbage looper, diamond back moth, tobacco budworm, corn earworm, beet armyworm, tobacco bollworm and the like. Crops which may be protected by the compound of the invention are lettuce, broccoli, corn, cabbage, cauliflower, tomato, cotton and so forth.

In practice, generally about 10 ppm to 10,000 ppm, preferably about 100 to 5,000 ppm of 2-(p-chlorophenyl) -4-chloro-1-(ethoxymethyl)-5-(trifluoromethyl) -pyrrole-3-carbonitrile dispersed in water or other suitable liquid carrier, is effective when applied to the crops or the soil in which the crops are growing to protect the crops from attack by insects, acarina and nematodes. The compound is also effective for protecting horticultural plants such as turf grass from attack by pests such as grubs, chinch bugs and the like.

While the 4-chloro-1-(ethoxymethyl)pyrrole compound of the invention is effective for controlling insects, acarina and nematodes when employed alone, it may also be used in combination with other pesticidal compounds including other nematocides and acaricides. For example, the compound of this invention may be employed effectively in combination with other arylpyrroles, phosphates, carbamates, pyrethroids, formamidines, chlorinated hydrocarbons, halobenzoylureas and the like.

In order to facilitate a further understanding of the present invention, the following examples are presented to illustrate more specific details thereof. The invention is not to be limited thereby except as defined in the claims. The term NMR designates nuclear magnetic resonance and the term HPLC designates high pressure liquid chromatography. Unless otherwise noted, all parts are by weight.

EXAMPLE 1

Preparation of
4-Chloro-1-(chloromethyl)-2-(p-chlorophenyl)
-5-(trifluoromethyl)pyrrole-3-carbonitrile

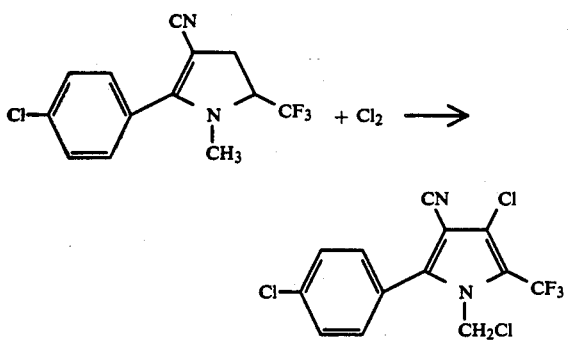

To a solution of 2-(p-chlorophenyl)-1-methyl -5-(trifluoromethyl)-2-pyrroline-3-carbonitrile (2.85 g, 0.01 mol) in chlorobenzene is added chlorine (0.8 g, 0.011 mol), stirred at room temperature for 1 hour, heated at 90° C. for 2 hours, cooled to room temperature, treated with additional chlorine (1.1 g, 0.015 mol), heated at 110° C. for 24 hours, cooled to room temperature, treated further with additional chlorine (1.4 g, 0.02 mol) and a catalytic amount of benzoyl peroxide and heated at 110° C. until reaction is complete by HPLC analysis. The mixture is cooled to room temperature, washed with aqueous sodium metabisulfite, dried (MgSO$_4$) and concentrated in vacuo to give a residue. The residue is recrystallized from heptane to give the title product as a white crystalline solid, mp 107–108° C.

EXAMPLE 2

Preparation of
4-Bromo-1-(bromomethyl)-2-(p-chlorophenyl)
-5-(trifluoromethyl)pyrrole-3-carbonitrile

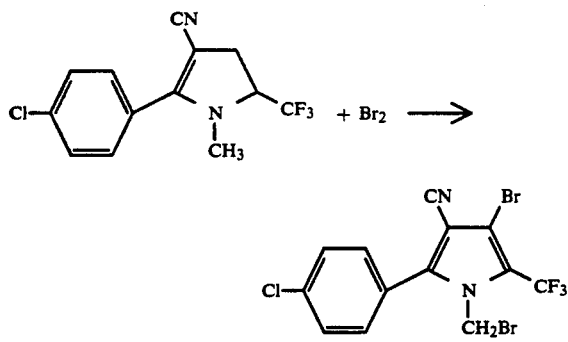

A stirred solution of 2-(p-chlorophenyl)-1-methyl-5-(trifluoromethyl)-2-pyrroline-3-carbonitrile (2.85 g, 0.01 mol) in carbon tetrachloride is treated with 1.1 molar equivalents of bromine at room temperature, heated at 70° C. for 2 hours, cooled to room temperature, treated with an additional 1.5 molar equivalents of bromine, heated at reflux temperature for 6–12 hours, cooled to room temperature, treated with a further 1.5 equivalents of bromine, irradiated for 2–4 days at 70° C. or until reaction is complete by HPLC analysis, cooled to room temperature and washed with aqueous sodium meta bisulfite. The organic phase is concentrated in vacuo to give a residue which is recrystallized from heptane to give the title product as white crystals, mp 131.0–131.5° C.

EXAMPLE 3

Preparation of
4-Chloro-2-(p-chlorophenyl)-1-(ethoxymethyl)
-5-(trifluoromethyl)pyrrole-3-carbonitrile

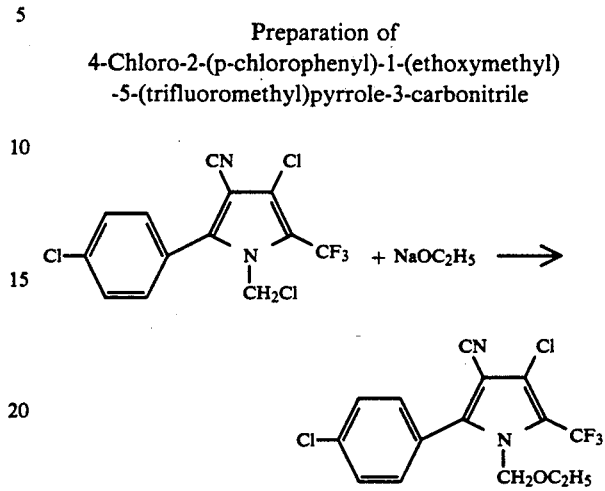

A solution of 4-chloro-1-(chloromethyl)-2-(p-chlorophenyl)-5-(trifluoromethyl)pyrrole-3-carbonitrile (2.6 g, 0.0074 mol) in tetrahydrofuran is treated with sodium ethoxide as a 21% wt/wt solution in denatured ethanol (3.6 mL, 0.0096 mol), stirred at room temperature for 1 hour, treated with an additional 2–3 drops of the sodium ethoxide solution, heated at reflux temperature for 1 hour, cooled and poured in water. The resultant precipitate is filtered, dried and recrystallized from isopropanol to afford the title product as a white solid, 1.6 g (60% yield), mp 104.0–104.5° C.

EXAMPLE 4

Preparation of
4-Bromo-1-(ethoxymethyl)-2-(p-chlorophenyl)
-5-(trifluoromethyl)pyrrole-3-carbonitrile

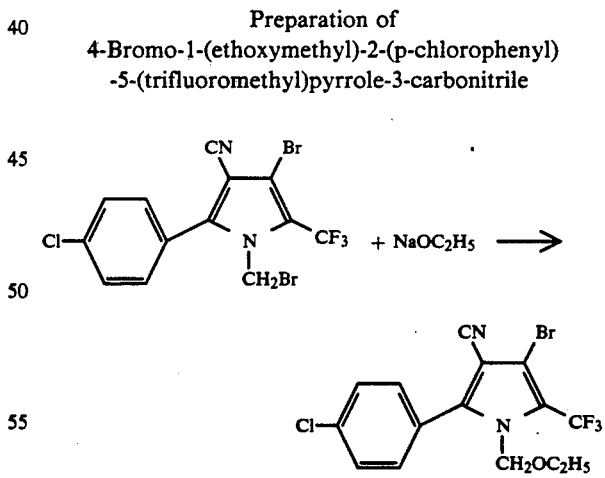

A mixture of 4-bromo-1-(bromomethyl)-2-nitrile (4.42 g, 0.01 mol) in absolute ethanol is treated with a 21% wt/wt ethanolic solution of sodium ethoxide (0.715 g, 0.011 mol), heated to 80° C. for 15–20 minutes, cooled to room temperature and diluted with water and ether. The organic phase is dried (MgSO$_4$) and concentrated in vacuo to give a solid residue which is recrystallized from heptane to give the title product as a white solid, 3.45 g (85% yield), mp 91–92° C.

EXAMPLE 5

Insecticide and Acaricide Evaluation

All tests are performed using technical material. All concentrations reported herein are in terms of active ingredient. All tests are kept at 27° C.

*Spodoptera eridania*, 3rd instar larvae, southern armyworm

A Sieva lima bean leaf expanded to 7-8 cm in length is dipped in the test suspension with agitation for 3 seconds and placed in a hood to dry. The leaf is then placed in a 100×10 mm petri dish containing a damp filter paper on the bottom and ten 3rd instar caterpillars. The dish is maintained for 5 days before observations are made of mortality, reduced feeding, or any interference with normal moulting.

*Spodoptera eridania*, 7 day residual

The plants treated in the above test are maintained under high intensity lamps in the greenhouse for 7 days. These lamps duplicate the effects of a bright sunny day in June in New Jersey and are kept on for 14 hour day length. After 7 days, the foliage is sampled and evaluated as described above.

*Tetranychus urticae(P-resistant strain)*, 2-spotted spider mite

Sieva lima bean plants with primary leaves expanded to 7-8 cm are selected, cut back to one plant per pot and infested with mites to obtain about 100 mites per leaf. The mite-infested plants are dipped in the test formulation for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Diabrotic undecimpunctate howardi*, 3rd instar southern corn rootworm

One cc of fine talc is placed in a 30 mL wide-mouth screw-top glass jar. One mL of the appropriate acetone suspension is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

*Aphis fabae*, mixed instar, bean aphid

Pots containing single nasturtium plants (Tropaeolum sp) about 5 cm tall are infested with about 100-200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Empoasca abrupts*, adults, western potato leafhopper

A Sieva lima bean leaf about 5 cm long is dipped in the test formulation for 3 seconds with agitation and placed in a hood to dry. The leaf is placed in a 100×10 mm petri dish containing a moist filter paper on the bottom. About 10 adjust leafhoppers are added to each dish and the treatments are kept for 3 days before mortality counts are made.

*Heliothis virescens*, 3rd instar tobacco budworm

Cotton cotyledons are dipped in the test formulation and allowed to dry in a hood. When dry, each is cut into quarters and ten sections placed individually in 30 mL plastic medicine cups containing a 5-7 mm long piece of damp dental wick. One third-instar caterpillar is added to each cup and a cardboard lid placed on the cup. Treatments are maintained for 3 days before mortality counts and estimates of reduction in feeding damage are made.

*Heliothis virescens*, egg, tobacco budworm

A young cotton leaf about 6-7 cm long is dipped in the test suspension with agitation for 3 seconds. Eggs are collected on cheesecloth which is cut into 10-20 mm squares containing about 50-100 eggs (6-30 hours old). A square of cheesecloth with eggs is also dipped in the test suspension and placed on the treated leaf. The combination is dried and placed in a cup (240 mL, 6 cm tall, top diameter 9.5 cm, bottom diameter 8 cm), into which a 5 cm length of damp dental wick has been placed. A clear plastic lid is placed on the cup and the treatments are held for 3 days before mortality counts are made.

*Blattella germanica*, bait test, adult male German cockroach

A 0.1% bait is prepared by pipetting a 1 mL of a 1,000 ppm solution of the test compound in acetone onto 1 gram of cornmeal in a 30 mL wide-moputh bottle. The bait is dried by passing a gentle stream of air into the bottle. The bait is placed in a 1 pint wide-mouth Mason jar and ten adult male cockroaches are added. A screen lid is placed on the jar and a small piece of cotton soaked in 10% honey is put on the top of the screen lid. Mortality counts are made after 3 days.

*Blattela germanica*, residue test, adult male German cockroach

One mL of a 1,000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

| Rating Scale: | |
|---|---|
| 0 = no effect | 5 = 56-65% kill |
| 1 = 10-25% kill | 6 = 66-75% kill |
| 2 = 26-35% kill | 7 = 76-85% kill |
| 3 = 36-45% kill | 8 = 86-99% kill |
| 4 = 46-55% kill | 9 = 100% kill |
| | R - reduced feeding |

The data obtained for the above-described evaluations are reported in Table I.

TABLE I

Insecticide and Acaricide Evaluation of 2-(p-chlorophenyl)-4-chloro-1-(ethoxymethyl)-5-(trifluoromethyl)pyrrole-3-carbonitrile

| | Evaluation | | | | |
|---|---|---|---|---|---|
| Test | 1,000 ppm | 100 ppm | 10 ppm | 1 ppm | 0.1 ppm |
| Southern Armyworm | | | | | |
| (3rd instar larvae) | 9 | 9 | 9 | 0 | — |
| (7 day residual) | 9 | 9 | 6 | — | — |
| 2-Spotted Spider Mite | — | — | 9 | 0 | — |

TABLE I-continued

Insecticide and Acaricide Evaluation of 2-(p-chloro-phenyl)-4-chloro-1-(ethoxymethyl)-5-(trifluoro-methyl)pyrrole-3-carbonitrile

| | | | | | |
|---|---|---|---|---|---|
| Bean Aphid | — | 9 | 4 | 0 | — |
| Leafhopper | — | 9 | 9 | 9 | — |
| Tobacco Budworm | | | | | |
| (Eggs) | 7 | 0 | — | — | — |
| (3rd instar) | 9 | 9 | 9 | — | — |
| German Cockroach | | | | | |
| (Bait) | 0 | — | — | — | — |
| (Residue) | 9 | 0 | — | — | — |
| | 50 kg/ha | | 10 kg/ha | | 1 kg/ha |
| Southern Corn Rootworm | 9 | | 7 | | 0 |

What is claimed is:

1. A process for the manufacture of a compound of formula I

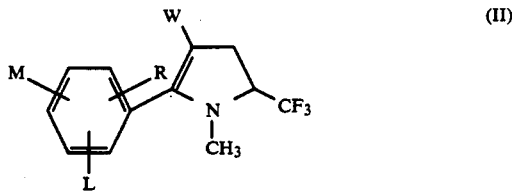

wherein
$R_1$ is $C_1-C_6$ alkyl;
W is CN, $NO_2$ or $CO_2R_2$;
X is Br, Cl or I;
L is hydrogen or halogen;
M and R are each independently hydrogen, $C_1-C_4$ alkyl, $C_1-C_4$ alkoxy, $C_1-C_4$ alkylsulfonyl, CN, $NO_2$, Cl, Br, F, I, $CF_3$, $R_3CF_2Z$ or $R_4CO$ and when M and R are on adjacent positions they may be taken together with the carbon atoms to which they are attached to form a ring in which MR represents the structure —OCH$_2$O—, —OCF$_2$O— or
—CH=CH—CH=CH—;

$R_2$ is $C_1-C_6$ alkyl, $C_3-C_6$ cycloalkyl or phenyl;
$R_3$ is hydrogen, F, $CHF_2$, CHFCl or $CF_3$;
$R_4$ is $C_1-C_4$ alkyl or $C_1-C_4$ alkoxy;
Z is $S(O)_n$ or O and
n is an integer of 0, 1 or 2 which comprises reacting a compound of formula II $$ \text{(II)} $$

wherein W, L, M and R are as described hereinabove with at least 1 equivalent of a halogen, wherein said halogen is bromine, chlorine or iodine, in the presence of a solvent to obtain a 2-aryl-1-methylpyrrole intermediate, reacting said 1-methylpyrrole intermediate with at least one additional molar equivalent of said halogen to form a 2-aryl-4-halo-1-methylpyrrole intermediate, reacting said 4-halo-1-methylpyrrole intermediate further with at least one molar equivalent of said halogen in the presence of a radical initiator to form a 2-aryl-4-halo-1-(halomethyl)pyrrole intermediate and reacting said 4-halo-1-(halomethyl)pyrrole intermediate with at least one molar equivalent of an alkali metal $C_1-C_6$-alkoxide to give the compound of formula I.

2. The process according to claim 1 wherein the reaction takes place at an elevated temperature.

3. The process according to claim 1 wherein X is Cl and the radical initiator is benzoyl peroxide.

4. The process according to claim 1 wherein X is Br and the radical initiator is light.

5. The process according to claim 1 wherein the solvent is selected from the group consisting of aromatic hydrocarbons, halogenated aromatic hydrocarbons and halogenated hydrocarbons.

6. The process according to claim 3 wherein the solvent is chlorobenzene.

7. The process according to claim 4 wherein the solvent is carbon tetrachloride.

8. The process according to claim 1 wherein the alkali metal $C_1-C_6$alkoxide is sodium ethoxide.

9. The process according to claim 1 wherein $R_1$ is ethyl, W is CN, L and R are hydrogen and M is halogen.

* * * * *